United States Patent [19]

Hickle et al.

[11] Patent Number: 5,262,399
[45] Date of Patent: * Nov. 16, 1993

[54] COMPOSITIONS AND METHODS FOR THE CONTROL OF FLUKES

[75] Inventors: Leslie A. Hickle, San Diego; August J. Sick, Oceanside; George E. Schwab, La Jolla; Kenneth E. Narva; Jewel M. Payne, both of San Diego, all of Calif.

[73] Assignee: Mycogen Corporation, San Diego, Calif.

[*] Notice: The portion of the term of this patent subsequent to Aug. 14, 2007 has been disclaimed.

[21] Appl. No.: 675,772

[22] Filed: Mar. 27, 1991

Related U.S. Application Data

[63] Continuation-in-part of Ser. No. 565,544, Aug. 10, 1990, abandoned, and a continuation-in-part of Ser. No. 557,246, Jul. 24, 1990, and a continuation-in-part of Ser. No. 558,738, Jul. 27, 1990, Pat. No. 5,151,363, said Ser. No. 565,544, is a continuation-in-part of Ser. No. 84,653, Aug. 12, 1987, Pat. No. 4,948,734, said Ser. No. 557,246, is a continuation-in-part of Ser. No. 535,810, Jun. 11, 1990, abandoned, which is a continuation-in-part of Ser. No. 84,653, Aug. 12, 1987, Pat. No. 4,948,734.

[51] Int. Cl.$^5$ .................. A61K 37/00; A01N 25/00
[52] U.S. Cl. .................................. 514/12; 424/93 L; 424/405; 530/350
[58] Field of Search ................ 424/93 L, 405; 514/2, 514/12; 435/172.3; 530/350

[56] References Cited

U.S. PATENT DOCUMENTS 4,948,734  8/1990  Edwards et al. ............... 435/252.5
5,093,120  3/1992  Edwards et al. ............... 424/93

OTHER PUBLICATIONS

Bottjer, K. P., L. W. Bone, S. S. Gill, (1985), "Nematoda: Susceptibility of the Egg to Bacillus thuringiensis Toxins", Exp. Parasitol., 60:239–244.

Ignoffo, C. M., V. H. Dropkin, (1977), "Deleterious Effects of the Thermostable Toxin of Bacillus thuringiensis on Species of Soil-Inhabiting, Myceliophagous, and Plant-Parasitic Nematodes", J. Kansas Entomological Soc., 50(3):394–398.

Ciordia, H., W. E. Bizzell, (1961), "A Preliminary Report of the Effects of Bacillus thuringiensis var. thuringienesis on the Development of the Free-Living Stages of Some Cattle Nematodes", J. Parasitol., 47:41 (abstract).

Primary Examiner—Robert A. Wax
Assistant Examiner—Keith D. Hendricks
Attorney, Agent, or Firm—Saliwanchik & Saliwanchik

[57] ABSTRACT

Methods and compositions for the control of flukes are described. Specifically, Bacillus thuringiensis (B.t.) isolates having flukicidal activity are disclosed. Also described are recombinant hosts which express B.t. genes coding for flukicidal toxins. The B.t. isolates and recombinant proteins are shown to be useful in a method for controlling flukes including the liver fluke.

9 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 4155 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17a ( v i i ) IMMEDIATE SOURCE:
( B ) CLONE: lambdagem (tm) - 11 Library of Kenneth Narva ( x i ) SEQUENCE DESCRIPTION: SEQ ID NO:1:

```
ATGGCAATTT TAAATGAATT ATATCCATCT GTACCTTATA ATGTATTGGC GTATACGCCA    60
CCCTCTTTTT TACCTGATGC GGGTACACAA GCTACACCTG CTGACTTAAC AGCTTATGAA   120
CAATTGTTGA AAAATTTAGA AAAAGGGATA AATGCTGGAA CTTATTCGAA AGCAATAGCT   180
GATGTACTTA AAGGTATTTT TATAGATGAT ACAATAAATT ATCAAACATA TGTAAATATT   240
GGTTTAAGTT TAATTACATT AGCTGTACCG GAAATTGGTA TTTTTACACC TTTCATCGGT   300
TTGTTTTTTG CTGCATTGAA TAAACATGAT GCTCCACCTC CTCCTAATGC AAAAGATATA   360
TTTGAGGCTA TGAAACCAGC GATTCAAGAG ATGATTGATA GAACTTTAAC TGCGGATGAG   420
CAAACATTTT TAAATGGGGA AATAAGTGGT TTACAAAATT TAGCAGCAAG ATACCAGTCT   480
ACAATGGATG ATATTCAAAG CCATGGAGGA TTTAATAAGG TAGATTCTGG ATTAATTAAA   540
AAGTTTACAG ATGAGGTACT ATCTTTAAAT AGTTTTTATA CAGATCGTTT ACCTGTATTT   600
ATTACAGATA ATACAGCGGA TCGAACTTTG TTAGGTCTTC CTTATTATGC TATACTTGCG   660
AGCATGCATC TTATGTTATT AAGAGATATC ATTACTAAGG GTCCGACATG GGATTCTAAA   720
ATTAATTTCA CACCAGATGC AATTGATTCC TTTAAAACCG ATATTAAAAA TAATATAAAG   780
CTTTACTCTA AAACTATTTA TGACGTATTT CAGAAGGGAC TTGCTTCATA CGGAACGCCT   840
TCTGATTTAG AGTCCTTTGC AAAAAAACAA AAATATATTG AAATTATGAC AACACATTGT   900
TTAGATTTTG CAAGATTGTT TCCTACTTTT GATCCAGATC TTTATCCAAC AGGATCAGGT   960
GATATAAGTT TACAAAAAAC ACGTAGAATT CTTTCTCCTT TTATCCCTAT ACGTACTGCA  1020
GATGGGTTAA CATTAAATAA TACTTCAATT GATACTTCAA ATTGGCCTAA TTATGAAAAT  1080
GGGAATGGCG CGTTTCCAAA CCCAAAAGAA AGAATATTAA AACAATTCAA ACTGTATCCT  1140
AGTTGGAGAG CGGGACAGTA CGGTGGGCTT TTACAACCTT ATTTATGGGC AATAGAAGTC  1200
CAAGATTCTG TAGAGACTCG TTTGTATGGG CAGCTTCCAG CTGTAGATCC ACAGGCAGGG  1260
CCTAATTATG TTTCCATAGA TTCTTCTAAT CCAATCATAC AAATAAATAT GGATACTTGG  1320
AAAACACCAC CACAAGGTGC GAGTGGGTGG AATACAAATT TAATGAGAGG AAGTGTAAGC  1380
GGGTTAAGTT TTTTACAACG AGATGGTACG AGACTTAGTG CTGGTATGGG TGGTGGTTTT  1440
GCTGATACAA TATATAGTCT CCCTGCAACT CATTATCTTT CTTATCTCTA TGGAACTCCT  1500
```

| | | | | | |
|---|---|---|---|---|---|
| TATCAAACTT | CTGATAACTA | TTCTGGTCAC | GTTGGTGCAT | TGGTAGGTGT | GAGTACGCCT | 1560 |
| CAAGAGGCTA | CTCTTCCTAA | TATTATAGGT | CAACCAGATG | AACAGGGAAA | TGTATCTACA | 1620 |
| ATGGATTTC | CGTTTGAAAA | AGCTTCTTAT | GGAGGTACAG | TTGTTAAAGA | ATGGTTAAAT | 1680 |
| GGTGCGAATG | CGATGAAGCT | TTCTCCTGGG | CAATCTATAG | GTATTCCTAT | TACAAATGTA | 1740 |
| ACAAGTGGAG | AATATCAAAT | TCGTTGTCGT | TATGCAAGTA | ATGATAATAC | TAACGTTTTC | 1800 |
| TTTAATGTAG | ATACTGGTGG | AGCAAATCCA | ATTTTCCAAC | AGATAAACTT | TGCATCTACT | 1860 |
| GTAGATAATA | ATACGGGAGT | ACAAGGAGCA | AATGGTGTCT | ATGTAGTCAA | ATCTATTGCT | 1920 |
| ACAACTGATA | ATTCTTTTAC | AGAAATTCCT | GCGAAGACGA | TTAATGTTCA | TTTAACCAAC | 1980 |
| CAAGGTTCTT | CTGATGTCTT | TTTAGACCGT | ATTGAATTTA | TACCTTTTTC | TCTACCTCTT | 2040 |
| ATATATCATG | GAAGTTATAA | TACTTCATCA | GGTGCAGATG | ATGTTTATG | GTCTTCTTCA | 2100 |
| AATATGAATT | ACTACGATAT | AATAGTAAAT | GGTCAGGCCA | ATAGTAGTAG | TATCGCTAGT | 2160 |
| TCTATGCATT | TGCTTAATAA | AGGAAAAGTG | ATAAAAACAA | TTGATATTCC | AGGGCATTCG | 2220 |
| GAAACCTTCT | TTGCTACGTT | CCCAGTTCCA | GAAGGATTTA | ATGAAGTTAG | AATTCTTGCT | 2280 |
| GGCCTTCCAG | AAGTTAGTGG | AAATATTACC | GTACAATCTA | ATAATCCGCC | TCAACCTAGT | 2340 |
| AATAATGGTG | GTGGTGATGG | TGGTGGTAAT | GGTGGTGGTG | ATGGTGGTCA | ATACAATTTT | 2400 |
| TCTTTAAGCG | GATCTGATCA | TACGACTATT | TATCATGGAA | AACTTGAAAC | TGGGATTCAT | 2460 |
| GTACAAGGTA | ATTATACCTA | TACAGGTACT | CCCGTATTAA | TACTGAATGC | TTACAGAAAT | 2520 |
| AATACTGTAG | TATCAAGCAT | TCCAGTATAT | TCTCCTTTTG | ATATAACTAT | ACAGACAGAA | 2580 |
| GCTGATAGCC | TTGAGCTTGA | ACTACAACCT | AGATATGGTT | TTGCCACAGT | GAATGGTACT | 2640 |
| GCAACAGTAA | AAGTCCTAA | TGTAAATTAC | GATAGATCAT | TTAAACTCCC | AATAGACTTA | 2700 |
| CAAAATATCA | CAACACAAGT | AAATGCATTA | TTCGCATCTG | GAACACAAAA | TATGCTTGCT | 2760 |
| CATAATGTAA | GTGATCATGA | TATTGAAGAA | GTTGTATTAA | AAGTGGATGC | CTTATCAGAT | 2820 |
| GAAGTATTTG | GAGATGAGAA | GAAGGCTTTA | CGTAAATTGG | TGAATCAAGC | AAAACGTTTG | 2880 |
| AGTAGAGCAA | GAAATCTTCT | GATAGGTGGG | AGTTTTGAAA | ATTGGGATGC | ATGGTATAAA | 2940 |
| GGAAGAAATG | TAGTAACTGT | ATCTGATCAT | GAACTATTTA | AGAGTGATCA | TGTATTATTA | 3000 |
| CCACCACCAG | GATTGTCTCC | ATCTTATATT | TTCCAAAAAG | TGGAGGAATC | TAAATTAAAA | 3060 |
| CCAAATACAC | GTTATATTGT | TTCTGGATTC | ATCGCACATG | GAAAAGACCT | AGAAATTGTT | 3120 |
| GTTTCACGTT | ATGGGCAAGA | AGTGCAAAAG | GTCGTGCAAG | TTCCTTATGG | AGAAGCATTC | 3180 |
| CCGTTAACAT | CAAATGGACC | AGTTTGTTGT | CCCCCACGTT | CTACAAGTAA | TGGAACCTTA | 3240 |
| GGAGATCCAC | ATTTCTTTAG | TTACAGTATC | GATGTAGGTG | CACTAGATTT | ACAAGCAAAC | 3300 |
| CCTGGTATTG | AATTTGGTCT | TCGTATTGTA | AATCCAACTG | AATGGCACG | CGTAAGCAAT | 3360 |
| TTGGAAATTC | GTGAAGATCG | TCCATTAGCA | GCAAATGAAA | TACGACAAGT | ACAACGTGTC | 3420 |
| GCAAGAAATT | GGAGAACCGA | GTATGAGAAA | GAACGTGCGG | AAGTAACAAG | TTTAATTCAA | 3480 |
| CCTGTTATCA | ATCGAATCAA | CGGATTGTAT | GAAAATGGAA | ATTGGAACGG | TTCTATTCGT | 3540 |
| TCAGATATTT | CGTATCAGAA | TATAGACGCG | ATTGTATTAC | CAACGTTACC | AAAGTTACGC | 3600 |
| CATTGGTTTA | TGTCAGATAG | ATTCAGTGAA | CAAGGAGATA | TAATGGCTAA | ATTCCAAGGT | 3660 |
| GCATTAAATC | GTGCGTATGC | ACAACTGGAA | CAAAGTACGC | TTCTGCATAA | TGGTCATTTT | 3720 |
| ACAAAAGATG | CAGCTAATTG | GACAATAGAA | GGCGATGCAC | ATCAGATAAC | ACTAGAAGAT | 3780 |
| GGTAGACGTG | TATTGCGACT | TCCAGATTGG | TCTTCGAGTG | TATCTCAAAT | GATTGAAATC | 3840 |
| GAGAATTTTA | ATCCAGATAA | AGAATACAAC | TTAGTATTCC | ATGGGCAAGG | AGAAGGAACG | 3900 |
| GTTACGTTGG | AGCATGGAGA | AGAAACAAAA | TATATAGAAA | CGCATACACA | TCATTTTGCG | 3960 |

```
AATTTTACAA  CTTCTCAACG  TCAAGGACTC  ACGTTTGAAT  CAAATAAAGT  GACAGTGACC    4020

ATTTCTTCAG  AAGATGGAGA  ATTCTTAGTG  GATAATATTG  CGCTTGTGGA  AGCTCCTCTT    4080

CCTACAGATG  ACCAAAATTC  TGAGGGAAAT  ACGGCTTCCA  GTACGAATAG  CGATACAAGT    4140

ATGAACAACA  ATCAA                                                        4155
```

( 2 ) INFORMATION FOR SEQ ID NO:2:

( i ) SEQUENCE CHARACTERISTICS:
        ( A ) LENGTH: 1385 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( C ) INDIVIDUAL ISOLATE: PS17

( v i i ) IMMEDIATE SOURCE:
        ( A ) LIBRARY: LAMBDAGEM (TM) - 11 LIBRARY OF KENNETH NARVA
        ( B ) CLONE: 17A ( x i ) SEQUENCE DESCRIPTION: SEQ ID NO:2:

```
Met  Ala  Ile  Leu  Asn  Glu  Leu  Tyr  Pro  Ser  Val  Pro  Tyr  Asn  Val  Leu
 1              5                        10                       15

Ala  Tyr  Thr  Pro  Pro  Ser  Phe  Leu  Pro  Asp  Ala  Gly  Thr  Gln  Ala  Thr
              20                       25                       30

Pro  Ala  Asp  Leu  Thr  Ala  Tyr  Glu  Gln  Leu  Leu  Lys  Asn  Leu  Glu  Lys
         35                       40                       45

Gly  Ile  Asn  Ala  Gly  Thr  Tyr  Ser  Lys  Ala  Ile  Ala  Asp  Val  Leu  Lys
    50                       55                       60

Gly  Ile  Phe  Ile  Asp  Asp  Thr  Ile  Asn  Tyr  Gln  Thr  Tyr  Val  Asn  Ile
65                       70                       75                       80

Gly  Leu  Ser  Leu  Ile  Thr  Leu  Ala  Val  Pro  Glu  Ile  Gly  Ile  Phe  Thr
                   85                       90                       95

Pro  Phe  Ile  Gly  Leu  Phe  Phe  Ala  Ala  Leu  Asn  Lys  His  Asp  Ala  Pro
              100                      105                      110

Pro  Pro  Pro  Asn  Ala  Lys  Asp  Ile  Phe  Glu  Ala  Met  Lys  Pro  Ala  Ile
         115                      120                      125

Gln  Glu  Met  Ile  Asp  Arg  Thr  Leu  Thr  Ala  Asp  Glu  Gln  Thr  Phe  Leu
    130                      135                      140

Asn  Gly  Glu  Ile  Ser  Gly  Leu  Gln  Asn  Leu  Ala  Ala  Arg  Tyr  Gln  Ser
145                      150                      155                      160

Thr  Met  Asp  Asp  Ile  Gln  Ser  His  Gly  Gly  Phe  Asn  Lys  Val  Asp  Ser
                   165                      170                      175

Gly  Leu  Ile  Lys  Lys  Phe  Thr  Asp  Glu  Val  Leu  Ser  Leu  Asn  Ser  Phe
              180                      185                      190

Tyr  Thr  Asp  Arg  Leu  Pro  Val  Phe  Ile  Thr  Asp  Asn  Thr  Ala  Asp  Arg
         195                      200                      205

Thr  Leu  Leu  Gly  Leu  Pro  Tyr  Tyr  Ala  Ile  Leu  Ala  Ser  Met  His  Leu
    210                      215                      220

Met  Leu  Leu  Arg  Asp  Ile  Ile  Thr  Lys  Gly  Pro  Thr  Trp  Asp  Ser  Lys
225                      230                      235                      240

Ile  Asn  Phe  Thr  Pro  Asp  Ala  Ile  Asp  Ser  Phe  Lys  Thr  Asp  Ile  Lys
                   245                      250                      255

Asn  Asn  Ile  Lys  Leu  Tyr  Ser  Lys  Thr  Ile  Tyr  Asp  Val  Phe  Gln  Lys
```

|     |     |     |     |     | 260 |     |     |     |     | 265 |     |     |     |     | 270 |     |     |
|-----|-----|-----|-----|-----|-----|-----|-----|-----|-----|-----|-----|-----|-----|-----|-----|-----|-----|

```
                            260                        265                        270
Gly  Leu  Ala  Ser  Tyr  Gly  Thr  Pro  Ser  Asp  Leu  Glu  Ser  Phe  Ala  Lys
          275                      280                      285
Lys  Gln  Lys  Tyr  Ile  Glu  Ile  Met  Thr  Thr  His  Cys  Leu  Asp  Phe  Ala
          290                      295                      300
Arg  Leu  Phe  Pro  Thr  Phe  Asp  Pro  Asp  Leu  Tyr  Pro  Thr  Gly  Ser  Gly
305                           310                      315                      320
Asp  Ile  Ser  Leu  Gln  Lys  Thr  Arg  Arg  Ile  Leu  Ser  Pro  Phe  Ile  Pro
                    325                      330                      335
Ile  Arg  Thr  Ala  Asp  Gly  Leu  Thr  Leu  Asn  Asn  Thr  Ser  Ile  Asp  Thr
                    340                      345                      350
Ser  Asn  Trp  Pro  Asn  Tyr  Glu  Asn  Gly  Asn  Gly  Ala  Phe  Pro  Asn  Pro
          355                      360                      365
Lys  Glu  Arg  Ile  Leu  Lys  Gln  Phe  Lys  Leu  Tyr  Pro  Ser  Trp  Arg  Ala
     370                      375                      380
Gly  Gln  Tyr  Gly  Gly  Leu  Leu  Gln  Pro  Tyr  Leu  Trp  Ala  Ile  Glu  Val
385                      390                      395                      400
Gln  Asp  Ser  Val  Glu  Thr  Arg  Leu  Tyr  Gly  Gln  Leu  Pro  Ala  Val  Asp
                         405                      410                      415
Pro  Gln  Ala  Gly  Pro  Asn  Tyr  Val  Ser  Ile  Asp  Ser  Ser  Asn  Pro  Ile
               420                      425                      430
Ile  Gln  Ile  Asn  Met  Asp  Thr  Trp  Lys  Thr  Pro  Pro  Gln  Gly  Ala  Ser
          435                      440                      445
Gly  Trp  Asn  Thr  Asn  Leu  Met  Arg  Gly  Ser  Val  Ser  Gly  Leu  Ser  Phe
     450                      455                      460
Leu  Gln  Arg  Asp  Gly  Thr  Arg  Leu  Ser  Ala  Gly  Met  Gly  Gly  Gly  Phe
465                      470                      475                      480
Ala  Asp  Thr  Ile  Tyr  Ser  Leu  Pro  Ala  Thr  His  Tyr  Leu  Ser  Tyr  Leu
               485                      490                      495
Tyr  Gly  Thr  Pro  Tyr  Gln  Thr  Ser  Asp  Asn  Tyr  Ser  Gly  His  Val  Gly
               500                      505                      510
Ala  Leu  Val  Gly  Val  Ser  Thr  Pro  Gln  Glu  Ala  Thr  Leu  Pro  Asn  Ile
          515                      520                      525
Ile  Gly  Gln  Pro  Asp  Glu  Gln  Gly  Asn  Val  Ser  Thr  Met  Gly  Phe  Pro
     530                      535                      540
Phe  Glu  Lys  Ala  Ser  Tyr  Gly  Gly  Thr  Val  Val  Lys  Glu  Trp  Leu  Asn
545                      550                      555                      560
Gly  Ala  Asn  Ala  Met  Lys  Leu  Ser  Pro  Gly  Gln  Ser  Ile  Gly  Ile  Pro
               565                      570                      575
Ile  Thr  Asn  Val  Thr  Ser  Gly  Glu  Tyr  Gln  Ile  Arg  Cys  Arg  Tyr  Ala
               580                      585                      590
Ser  Asn  Asp  Asn  Thr  Asn  Val  Phe  Phe  Asn  Val  Asp  Thr  Gly  Gly  Ala
          595                      600                      605
Asn  Pro  Ile  Phe  Gln  Gln  Ile  Asn  Phe  Ala  Ser  Thr  Val  Asp  Asn  Asn
     610                      615                      620
Thr  Gly  Val  Gln  Gly  Ala  Asn  Gly  Val  Tyr  Val  Lys  Ser  Ile  Ala
625                      630                      635                      640
Thr  Thr  Asp  Asn  Ser  Phe  Thr  Glu  Ile  Pro  Ala  Lys  Thr  Ile  Asn  Val
                    645                      650                      655
His  Leu  Thr  Asn  Gln  Gly  Ser  Ser  Asp  Val  Phe  Leu  Asp  Arg  Ile  Glu
                    660                      665                      670
Phe  Ile  Pro  Phe  Ser  Leu  Pro  Leu  Ile  Tyr  His  Gly  Ser  Tyr  Asn  Thr
               675                      680                      685
Ser  Ser  Gly  Ala  Asp  Asp  Val  Leu  Trp  Ser  Ser  Asn  Met  Asn  Tyr
     690                      695                      700
```

```
Tyr  Asp  Ile  Ile  Val  Asn  Gly  Gln  Ala  Asn  Ser  Ser  Ser  Ile  Ala  Ser
705                      710                      715                      720

Ser  Met  His  Leu  Leu  Asn  Lys  Gly  Lys  Val  Ile  Lys  Thr  Ile  Asp  Ile
                    725                      730                      735

Pro  Gly  His  Ser  Glu  Thr  Phe  Phe  Ala  Thr  Phe  Pro  Val  Pro  Glu  Gly
               740                      745                      750

Phe  Asn  Glu  Val  Arg  Ile  Leu  Ala  Gly  Leu  Pro  Glu  Val  Ser  Gly  Asn
          755                      760                      765

Ile  Thr  Val  Gln  Ser  Asn  Asn  Pro  Pro  Gln  Pro  Ser  Asn  Asn  Gly  Gly
     770                      775                      780

Gly  Asp  Gly  Gly  Gly  Asn  Gly  Gly  Gly  Asp  Gly  Gly  Gln  Tyr  Asn  Phe
785                      790                      795                      800

Ser  Leu  Ser  Gly  Ser  Asp  His  Thr  Thr  Ile  Tyr  His  Gly  Lys  Leu  Glu
               805                      810                      815

Thr  Gly  Ile  His  Val  Gln  Gly  Asn  Tyr  Thr  Tyr  Thr  Gly  Thr  Pro  Val
               820                      825                      830

Leu  Ile  Leu  Asn  Ala  Tyr  Arg  Asn  Asn  Thr  Val  Val  Ser  Ser  Ile  Pro
          835                      840                      845

Val  Tyr  Ser  Pro  Phe  Asp  Ile  Thr  Ile  Gln  Thr  Glu  Ala  Asp  Ser  Leu
     850                      855                      860

Glu  Leu  Glu  Leu  Gln  Pro  Arg  Tyr  Gly  Phe  Ala  Thr  Val  Asn  Gly  Thr
865                      870                      875                      880

Ala  Thr  Val  Lys  Ser  Pro  Asn  Val  Asn  Tyr  Asp  Arg  Ser  Phe  Lys  Leu
                    885                      890                      895

Pro  Ile  Asp  Leu  Gln  Asn  Ile  Thr  Thr  Gln  Val  Asn  Ala  Leu  Phe  Ala
               900                      905                      910

Ser  Gly  Thr  Gln  Asn  Met  Leu  Ala  His  Asn  Val  Ser  Asp  His  Asp  Ile
               915                      920                      925

Glu  Glu  Val  Val  Leu  Lys  Val  Asp  Ala  Leu  Ser  Asp  Glu  Val  Phe  Gly
930                      935                      940

Asp  Glu  Lys  Lys  Ala  Leu  Arg  Lys  Leu  Val  Asn  Gln  Ala  Lys  Arg  Leu
945                      950                      955                      960

Ser  Arg  Ala  Arg  Asn  Leu  Leu  Ile  Gly  Gly  Ser  Phe  Glu  Asn  Trp  Asp
                    965                      970                      975

Ala  Trp  Tyr  Lys  Gly  Arg  Asn  Val  Val  Thr  Val  Ser  Asp  His  Glu  Leu
               980                      985                      990

Phe  Lys  Ser  Asp  His  Val  Leu  Leu  Pro  Pro  Pro  Gly  Leu  Ser  Pro  Ser
          995                      1000                     1005

Tyr  Ile  Phe  Gln  Lys  Val  Glu  Glu  Ser  Lys  Leu  Lys  Pro  Asn  Thr  Arg
     1010                     1015                     1020

Tyr  Ile  Val  Ser  Gly  Phe  Ile  Ala  His  Gly  Lys  Asp  Leu  Glu  Ile  Val
     1025                     1030                     1035                     1040

Val  Ser  Arg  Tyr  Gly  Gln  Glu  Val  Gln  Lys  Val  Val  Gln  Val  Pro  Tyr
               1045                     1050                     1055

Gly  Glu  Ala  Phe  Pro  Leu  Thr  Ser  Asn  Gly  Pro  Val  Cys  Cys  Pro  Pro
               1060                     1065                     1070

Arg  Ser  Thr  Ser  Asn  Gly  Thr  Leu  Gly  Asp  Pro  His  Phe  Phe  Ser  Tyr
          1075                     1080                     1085

Ser  Ile  Asp  Val  Gly  Ala  Leu  Asp  Leu  Gln  Ala  Asn  Pro  Gly  Ile  Glu
          1090                     1095                     1100

Phe  Gly  Leu  Arg  Ile  Val  Asn  Pro  Thr  Gly  Met  Ala  Arg  Val  Ser  Asn
1105                     1110                     1115                     1120

Leu  Glu  Ile  Arg  Glu  Asp  Arg  Pro  Leu  Ala  Ala  Asn  Glu  Ile  Arg  Gln
               1125                     1130                     1135
```

|     |     |     |     |     |     |     |     |     |     |     |     |     |     |
| --- | --- | --- | --- | --- | --- | --- | --- | --- | --- | --- | --- | --- | --- |
| Val | Gln | Arg | Val | Ala | Arg | Asn | Trp | Arg | Thr | Glu | Tyr | Glu | Lys | Glu | Arg |
|     |     |     | 1140 |     |     |     | 1145 |     |     |     |     | 1150 |     |
| Ala | Glu | Val | Thr | Ser | Leu | Ile | Gln | Pro | Val | Ile | Asn | Arg | Ile | Asn | Gly |
|     |     |     | 1155 |     |     |     | 1160 |     |     |     |     | 1165 |     |
| Leu | Tyr | Glu | Asn | Gly | Asn | Trp | Asn | Gly | Ser | Ile | Arg | Ser | Asp | Ile | Ser |
|     |     |     | 1170 |     |     |     | 1175 |     |     |     |     | 1180 |     |
| Tyr | Gln | Asn | Ile | Asp | Ala | Ile | Val | Leu | Pro | Thr | Leu | Pro | Lys | Leu | Arg |
| 1185 |     |     |     | 1190 |     |     |     |     | 1195 |     |     |     |     | 1200 |
| His | Trp | Phe | Met | Ser | Asp | Arg | Phe | Ser | Glu | Gln | Gly | Asp | Ile | Met | Ala |
|     |     |     |     | 1205 |     |     |     |     | 1210 |     |     |     |     | 1215 |
| Lys | Phe | Gln | Gly | Ala | Leu | Asn | Arg | Ala | Tyr | Ala | Gln | Leu | Glu | Gln | Ser |
|     |     |     | 1220 |     |     |     |     | 1225 |     |     |     |     | 1230 |     |
| Thr | Leu | Leu | His | Asn | Gly | His | Phe | Thr | Lys | Asp | Ala | Ala | Asn | Trp | Thr |
|     |     |     | 1235 |     |     |     |     | 1240 |     |     |     | 1245 |     |     |
| Ile | Glu | Gly | Asp | Ala | His | Gln | Ile | Thr | Leu | Glu | Asp | Gly | Arg | Arg | Val |
|     |     |     | 1250 |     |     |     |     | 1255 |     |     |     | 1260 |     |     |
| Leu | Arg | Leu | Pro | Asp | Trp | Ser | Ser | Val | Ser | Gln | Met | Ile | Glu | Ile |
| 1265 |     |     |     | 1270 |     |     |     |     | 1275 |     |     |     |     | 1280 |
| Glu | Asn | Phe | Asn | Pro | Asp | Lys | Glu | Tyr | Asn | Leu | Val | Phe | His | Gly | Gln |
|     |     |     |     | 1285 |     |     |     |     | 1290 |     |     |     |     | 1295 |
| Gly | Glu | Gly | Thr | Val | Thr | Leu | Glu | His | Gly | Glu | Glu | Thr | Lys | Tyr | Ile |
|     |     |     | 1300 |     |     |     |     | 1305 |     |     |     | 1310 |     |     |
| Glu | Thr | His | Thr | His | His | Phe | Ala | Asn | Phe | Thr | Thr | Ser | Gln | Arg | Gln |
|     |     |     | 1315 |     |     |     |     | 1320 |     |     |     | 1325 |     |     |
| Gly | Leu | Thr | Phe | Glu | Ser | Asn | Lys | Val | Thr | Val | Thr | Ile | Ser | Ser | Glu |
|     |     |     | 1330 |     |     |     |     | 1335 |     |     |     | 1340 |     |     |
| Asp | Gly | Glu | Phe | Leu | Val | Asp | Asn | Ile | Ala | Leu | Val | Glu | Ala | Pro | Leu |
| 1345 |     |     |     | 1350 |     |     |     |     | 1355 |     |     |     |     | 1360 |
| Pro | Thr | Asp | Asp | Gln | Asn | Ser | Glu | Gly | Asn | Thr | Ala | Ser | Ser | Thr | Asn |
|     |     |     |     | 1365 |     |     |     |     | 1370 |     |     |     | 1375 |     |
| Ser | Asp | Thr | Ser | Met | Asn | Asn | Asn | Gln |     |     |     |     |     |     |     |
|     |     |     | 1380 |     |     |     | 1385 |     |     |     |     |     |     |     |     |

( 2 ) INFORMATION FOR SEQ ID NO:3:

( i ) SEQUENCE CHARACTERISTICS:
        ( A ) LENGTH: 3867 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: PS17
        ( C ) INDIVIDUAL ISOLATE: PS17b ( v i i ) IMMEDIATE SOURCE:
( B ) CLONE: lambdagem (tm) - 11 Library of Kenneth Narva ( x i ) SEQUENCE DESCRIPTION: SEQ ID NO:4:

ATGGCAATTT TAAATGAATT ATATCCATCT GTACCTTATA ATGTATTGGC GTATACGCCA 60

CCCTCTTTTT TACCTGATGC GGGTACACAA GCTACACCTG CTGACTTAAC AGCTTATGAA 120

CAATTGTTGA AAAATTTAGA AAAAGGGATA AATGCTGGAA CTTATTCGAA AGCAATAGCT 180

GATGTACTTA AAGGTATTTT TATAGATGAT ACAATAAATT ATCAAACATA TGTAAATATT 240

GGTTTAAGTT TAATTACATT AGCTGTACCG GAAATTGGTA TTTTTACACC TTTCATCGGT 300

| | | | | | |
|---|---|---|---|---|---|
| TTGTTTTTTG | CTGCATTGAA | TAAACATGAT | GCTCCACCTC | CTCCTAATGC | AAAAGATATA | 360
| TTTGAGGCTA | TGAAACCAGC | GATTCAAGAG | ATGATTGATA | GAACTTTAAC | TGCGGATGAG | 420
| CAAACATTTT | TAAATGGGGA | AATAAGTGGT | TTACAAAATT | TAGCAGCAAG | ATACCAGTCT | 480
| ACAATGGATG | ATATTCAAAG | CCATGGAGGA | TTTAATAAGG | TAGATTCTGG | ATTAATTAAA | 540
| AAGTTTACAG | ATGAGGTACT | ATCTTTAAAT | AGTTTTTATA | CAGATCGTTT | ACCTGTATTT | 600
| ATTACAGATA | ATACAGCGGA | TCGAACTTTG | TTAGGTCTTC | CTTATTATGC | TATACTTGCG | 660
| AGCATGCATC | TTATGTTATT | AAGAGATATC | ATTACTAAGG | GTCCGACATG | GGATTCTAAA | 720
| ATTAATTTCA | CACCAGATGC | AATTGATTCC | TTTAAAACCG | ATATTAAAAA | TAATATAAAG | 780
| CTTTACTCTA | AAACTATTTA | TGACGTATTT | CAGAAGGGAC | TTGCTTCATA | CGGAACGCCT | 840
| TCTGATTTAG | AGTCCTTTGC | AAAAAAACAA | AAATATATTG | AAATTATGAC | AACACATTGT | 900
| TTAGATTTTG | CAAGATTGTT | TCCTACTTTT | GATCCAGATC | TTTATCCAAC | AGGATCAGGT | 960
| GATATAAGTT | TACAAAAAAC | ACGTAGAATT | CTTTCTCCTT | TATCCCTAT | ACGTACTGCA | 1020
| GATGGGTTAA | CATTAAATAA | TACTTCAATT | GATACTTCAA | ATTGGCCTAA | TTATGAAAAT | 1080
| GGGAATGGCG | CGTTTCCAAA | CCCAAAAGAA | AGAATATTAA | AACAATTCAA | ACTGTATCCT | 1140
| AGTTGGAGAG | CGGCACAGTA | CGGTGGGCTT | TTACAACCTT | ATTTATGGGC | AATAGAAGTC | 1200
| CAAGATTCTG | TAGAGACTCG | TTTGTATGGG | CAGCTTCCAG | CTGTAGATCC | ACAGGCAGGG | 1260
| CCTAATTATG | TTTCCATAGA | TTCTTCTAAT | CCAATCATAC | AAATAAATAT | GGATACTTGG | 1320
| AAAACACCAC | CACAAGGTGC | GAGTGGGTGG | AATACAAATT | TAATGAGAGG | AAGTGTAAGC | 1380
| GGGTTAAGTT | TTTTACAACG | AGATGGTACG | AGACTTAGTG | CTGGTATGGG | TGGTGGTTTT | 1440
| GCTGATACAA | TATATAGTCT | CCCTGCAACT | CATTATCTTT | CTTATCTCTA | TGGAACTCCT | 1500
| TATCAAACTT | CTGATAACTA | TTCTGGTCAC | GTTGGTGCAT | TGGTAGGTGT | GAGTACGCCT | 1560
| CAAGAGGCTA | CTCTTCCTAA | TATTATAGGT | CAACCAGATG | AACAGGGAAA | TGTATCTACA | 1620
| ATGGGATTTC | CGTTTGAAAA | AGCTTCTTAT | GGAGGTACAG | TTGTTAAAGA | ATGGTTAAAT | 1680
| GGTGCGAATG | CGATGAAGCT | TTCTCCTGGG | CAATCTATAG | GTATTCCTAT | TACAAATGTA | 1740
| ACAAGTGGAG | AATATCAAAT | TCGTTGTCGT | TATGCAAGTA | ATGATAATAC | TAACGTTTTC | 1800
| TTTAATGTAG | ATACTGGTGG | AGCAAATCCA | ATTTTCCAAC | AGATAAACTT | TGCATCTACT | 1860
| GTAGATAATA | ATACGGGAGT | ACAAGGAGCA | AATGGTGTCT | ATGTAGTCAA | ATCTATTGCT | 1920
| ACAACTGATA | ATTCTTTTAC | AGTAAAAATT | CCTGCGAAGA | CGATTAATGT | TCATTTAACC | 1980
| AACCAAGGTT | CTTCTGATGT | CTTTTTAGAT | CGTATTGAGT | TTGTTCCAAT | TCTAGAATCA | 2040
| AATACTGTAA | CTATATTCAA | CAATTCATAT | ACTACAGGTT | CAGCAAATCT | TATACCAGCA | 2100
| ATAGCTCCTC | TTTGGAGTAC | TAGTTCAGAT | AAAGCCCTTA | CAGGTTCTAT | GTCAATAACA | 2160
| GGTCGAACTA | CCCCTAACAG | TGATGATGCT | TTGCTTCGAT | TTTTTAAAAC | TAATTATGAT | 2220
| ACACAAACCA | TTCCTATTCC | GGGTTCCGGA | AAAGATTTTA | CAAATACTCT | AGAAATACAA | 2280
| GACATAGTTT | CTATTGATAT | TTTTGTCGGA | TCTGGTCTAC | ATGGATCCGA | TGGATCTATA | 2340
| AAATTAGATT | TTACCAATAA | TAATAGTGGT | AGTGGTGGCT | CTCCAAAGAG | TTTCACCGAG | 2400
| CAAAATGATT | TAGAGAATAT | CACAACACAA | GTGAATGCTC | TATTCACATC | TAATACACAA | 2460
| GATGCACTTG | CAACAGATGT | GAGTGATCAT | GATATTGAAG | AAGTGGTTCT | AAAAGTAGAT | 2520
| GCATTATCTG | ATGAAGTGTT | TGGAAAAGAG | AAAAAAACAT | TGCGTAAATT | TGTAAATCAA | 2580
| GCGAAGCGCT | TAAGCAAGGC | GCGTAATCTC | CTGGTAGGAG | GCAATTTTGA | TAACTTGGAT | 2640
| GCTTGGTATA | GAGGAAGAAA | TGTAGTAAAC | GTATCTAATC | ACGAACTGTT | GAAGAGTGAT | 2700
| CATGTATTAT | TACCACCACC | AGGATTGTCT | CCATCTTATA | TTTTCCAAAA | AGTGGAGGAA | 2760

-continued

```
TCTAAATTAA AACGAAATAC ACGTTATACG GTTTCTGGAT TTATTGCGCA TGCAACAGAT 2820
TTAGAAATTG TGGTTTCTCG TTATGGGCAA GAAATAAAGA AAGTGGTGCA AGTTCCTTAT 2880
GGAGAAGCAT TCCCATTAAC ATCAAGTGGA CCAGTTTGTT GTATCCCACA TTCTACAAGT 2940
AATGGAACTT TAGGCAATCC ACATTTCTTT AGTTACAGTA TTGATGTAGG TGCATTAGAT 3000
GTAGACACAA ACCCTGGTAT TGAATTCGGT CTTCGTATTG TAAATCCAAC TGGAATGGCA 3060
CGCGTAAGCA ATTTGGAAAT TCGTGAAGAT CGTCCATTAG CAGCAAATGA AATACGACAA 3120
GTACAACGTG TCGCAAGAAA TTGGAGAACC GAGTATGAGA AAGAACGTGC GGAAGTAACA 3180
AGTTTAATTC AACCTGTTAT CAATCGAATC AATGGATTGT ATGACAATGG AAATTGGAAC 3240
GGTTCTATTC GTTCAGATAT TTCGTATCAG AATATAGACG CGATTGTATT ACCAACGTTA 3300
CCAAAGTTAC GCCATTGGTT TATGTCAGAT AGATTTAGTG AACAAGGAGA TATCATGGCT 3360
AAATTCCAAG GTGCATTAAA TCGTGCGTAT GCACAACTGG AACAAAATAC GCTTCTGCAT 3420
AATGGTCATT TTACAAAAGA TGCAGCCAAT TGGACGGTAG AAGGCGATGC ACATCAGGTA 3480
GTATTAGAAG ATGGTAAACG TGTATTACGA TTGCCAGATT GGTCTTCGAG TGTGTCTCAA 3540
ACGATTGAAA TCGAGAATTT TGATCCAGAT AAAGAATATC AATTAGTATT TCATGGGCAA 3600
GGAGAAGGAA CGGTTACGTT GGAGCATGGA GAAGAAACAA AATATATAGA AACGCATACA 3660
CATCATTTTG CGAATTTTAC AACTTCTCAA CGTCAAGGAC TCACGTTTGA ATCAAATAAA 3720
GTGACAGTGA CCATTTCTTC AGAAGATGGA GAATTCTTAG TGGATAATAT TGCGCTTGTG 3780
GAAGCTCCTC TTCCTACAGA TGACCAAAAT TCTGAGGGAA ATACGGCTTC CAGTACGAAT 3840
AGCGATACAA GTATGAACAA CAATCAA                                    3867
```

( 2 ) INFORMATION FOR SEQ ID NO:4:

( i ) SEQUENCE CHARACTERISTICS:
( A ) LENGTH: 1289 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS17

( v i i ) IMMEDIATE SOURCE:
( A ) LIBRARY: LAMBDAGEM (TM) - 11 LIBRARY OF KENNETH NARVA
( B ) CLONE: 17B ( x i ) SEQUENCE DESCRIPTION: SEQ ID NO:5:

```
Met Ala Ile Leu Asn Glu Leu Tyr Pro Ser Val Pro Tyr Asn Val Leu
1               5                   10                  15

Ala Tyr Thr Pro Pro Ser Phe Leu Pro Asp Ala Gly Thr Gln Ala Thr
            20                  25                  30

Pro Ala Asp Leu Thr Ala Tyr Glu Gln Leu Leu Lys Asn Leu Glu Lys
        35                  40                  45

Gly Ile Asn Ala Gly Thr Tyr Ser Lys Ala Ile Ala Asp Val Leu Lys
    50                  55                  60

Gly Ile Phe Ile Asp Asp Thr Ile Asn Tyr Gln Thr Tyr Val Asn Ile
65                  70                  75                  80

Gly Leu Ser Leu Ile Thr Leu Ala Val Pro Glu Ile Gly Ile Phe Thr
                85                  90                  95
```

```
Pro  Phe  Ile  Gly  Leu  Phe  Phe  Ala  Ala  Leu  Asn  Lys  His  Asp  Ala  Pro
               100                 105                      110

Pro  Pro  Pro  Asn  Ala  Lys  Asp  Ile  Phe  Glu  Ala  Met  Lys  Pro  Ala  Ile
               115                 120                      125

Gln  Glu  Met  Ile  Asp  Arg  Thr  Leu  Thr  Ala  Asp  Glu  Gln  Thr  Phe  Leu
               130                 135                      140

Asn  Gly  Glu  Ile  Ser  Gly  Leu  Gln  Asn  Leu  Ala  Ala  Arg  Tyr  Gln  Ser
145                      150                      155                      160

Thr  Met  Asp  Asp  Ile  Gln  Ser  His  Gly  Gly  Phe  Asn  Lys  Val  Asp  Ser
               165                      170                      175

Gly  Leu  Ile  Lys  Lys  Phe  Thr  Asp  Glu  Val  Leu  Ser  Leu  Asn  Ser  Phe
               180                 185                      190

Tyr  Thr  Asp  Arg  Leu  Pro  Val  Phe  Ile  Thr  Asp  Asn  Thr  Ala  Asp  Arg
          195                 200                      205

Thr  Leu  Leu  Gly  Leu  Pro  Tyr  Tyr  Ala  Ile  Leu  Ala  Ser  Met  His  Leu
     210                      215                      220

Met  Leu  Leu  Arg  Asp  Ile  Ile  Thr  Lys  Gly  Pro  Thr  Trp  Asp  Ser  Lys
225                      230                 235                           240

Ile  Asn  Phe  Thr  Pro  Asp  Ala  Ile  Asp  Ser  Phe  Lys  Thr  Asp  Ile  Lys
               245                      250                      255

Asn  Asn  Ile  Lys  Leu  Tyr  Ser  Lys  Thr  Ile  Tyr  Asp  Val  Phe  Gln  Lys
               260                 265                      270

Gly  Leu  Ala  Ser  Tyr  Gly  Thr  Pro  Ser  Asp  Leu  Glu  Ser  Phe  Ala  Lys
          275                      280                      285

Lys  Gln  Lys  Tyr  Ile  Glu  Ile  Met  Thr  Thr  His  Cys  Leu  Asp  Phe  Ala
     290                      295                      300

Arg  Leu  Phe  Pro  Thr  Phe  Asp  Pro  Asp  Leu  Tyr  Pro  Thr  Gly  Ser  Gly
305                      310                      315                      320

Asp  Ile  Ser  Leu  Gln  Lys  Thr  Arg  Arg  Ile  Leu  Ser  Pro  Phe  Ile  Pro
               325                      330                      335

Ile  Arg  Thr  Ala  Asp  Gly  Leu  Thr  Leu  Asn  Asn  Thr  Ser  Ile  Asp  Thr
               340                 345                      350

Ser  Asn  Trp  Pro  Asn  Tyr  Glu  Asn  Gly  Asn  Gly  Ala  Phe  Pro  Asn  Pro
               355                      360                 365

Lys  Glu  Arg  Ile  Leu  Lys  Gln  Phe  Lys  Leu  Tyr  Pro  Ser  Trp  Arg  Ala
     370                      375                 380

Ala  Gln  Tyr  Gly  Gly  Leu  Leu  Gln  Pro  Tyr  Leu  Trp  Ala  Ile  Glu  Val
385                      390                      395                      400

Gln  Asp  Ser  Val  Glu  Thr  Arg  Leu  Tyr  Gly  Gln  Leu  Pro  Ala  Val  Asp
               405                      410                      415

Pro  Gln  Ala  Gly  Pro  Asn  Tyr  Val  Ser  Ile  Asp  Ser  Ser  Asn  Pro  Ile
               420                      425                      430

Ile  Gln  Ile  Asn  Met  Asp  Thr  Trp  Lys  Thr  Pro  Pro  Gln  Gly  Ala  Ser
               435                      440                      445

Gly  Trp  Asn  Thr  Asn  Leu  Met  Arg  Gly  Ser  Val  Ser  Gly  Leu  Ser  Phe
     450                      455                      460

Leu  Gln  Arg  Asp  Gly  Thr  Arg  Leu  Ser  Ala  Gly  Met  Gly  Gly  Gly  Phe
465                      470                      475                      480

Ala  Asp  Thr  Ile  Tyr  Ser  Leu  Pro  Ala  Thr  His  Tyr  Leu  Ser  Tyr  Leu
               485                      490                      495

Tyr  Gly  Thr  Pro  Tyr  Gln  Thr  Ser  Asp  Asn  Tyr  Ser  Gly  His  Val  Gly
               500                      505                      510

Ala  Leu  Val  Gly  Val  Ser  Thr  Pro  Gln  Glu  Ala  Thr  Leu  Pro  Asn  Ile
               515                      520                      525

Ile  Gly  Gln  Pro  Asp  Glu  Gln  Gly  Asn  Val  Ser  Thr  Met  Gly  Phe  Pro
```

-continued

|     | 530 |     |     |     | 535 |     |     |     | 540 |     |     |     |     |
|---|---|---|---|---|---|---|---|---|---|---|---|---|---|

Phe Glu Lys Ala Ser Tyr Gly Gly Thr Val Val Lys Glu Trp Leu Asn
545                     550                 555                 560

Gly Ala Asn Ala Met Lys Leu Ser Pro Gly Ser Ile Gly Ile Pro
                565             570                 575

Ile Thr Asn Val Thr Ser Gly Glu Tyr Gln Ile Arg Cys Arg Tyr Ala
            580             585                 590

Ser Asn Asp Asn Thr Asn Val Phe Phe Asn Val Asp Thr Gly Gly Ala
        595             600             605

Asn Pro Ile Phe Gln Gln Ile Asn Phe Ala Ser Thr Val Asp Asn Asn
    610             615             620

Thr Gly Val Gln Gly Ala Asn Gly Val Tyr Val Lys Ser Ile Ala
625             630             635             640

Thr Thr Asp Asn Ser Phe Thr Val Lys Ile Pro Ala Lys Thr Ile Asn
            645             650             655

Val His Leu Thr Asn Gln Gly Ser Ser Asp Val Phe Leu Asp Arg Ile
        660             665             670

Glu Phe Val Pro Ile Leu Glu Ser Asn Thr Val Thr Ile Phe Asn Asn
        675             680             685

Ser Tyr Thr Thr Gly Ser Ala Asn Leu Ile Pro Ala Ile Ala Pro Leu
    690             695             700

Trp Ser Thr Ser Ser Asp Lys Ala Leu Thr Gly Ser Met Ser Ile Thr
705             710             715             720

Gly Arg Thr Thr Pro Asn Ser Asp Asp Ala Leu Leu Arg Phe Phe Lys
            725             730             735

Thr Asn Tyr Asp Thr Gln Thr Ile Pro Ile Pro Gly Ser Gly Lys Asp
            740             745             750

Phe Thr Asn Thr Leu Glu Ile Gln Asp Ile Val Ser Ile Asp Ile Phe
        755             760             765

Val Gly Ser Gly Leu His Gly Ser Asp Gly Ser Ile Lys Leu Asp Phe
770             775             780

Thr Asn Asn Asn Ser Gly Ser Gly Gly Ser Pro Lys Ser Phe Thr Glu
785             790             795             800

Gln Asn Asp Leu Glu Asn Ile Thr Thr Gln Val Asn Ala Leu Phe Thr
            805             810             815

Ser Asn Thr Gln Asp Ala Leu Ala Thr Asp Val Ser Asp His Asp Ile
        820             825             830

Glu Glu Val Val Leu Lys Val Asp Ala Leu Ser Asp Glu Val Phe Gly
        835             840             845

Lys Glu Lys Lys Thr Leu Arg Lys Phe Val Asn Gln Ala Lys Arg Leu
850             855             860

Ser Lys Ala Arg Asn Leu Leu Val Gly Gly Asn Phe Asp Asn Leu Asp
865             870             875             880

Ala Trp Tyr Arg Gly Arg Asn Val Val Asn Val Ser Asn His Glu Leu
            885             890             895

Leu Lys Ser Asp His Val Leu Leu Pro Pro Pro Gly Leu Ser Pro Ser
            900             905             910

Tyr Ile Phe Gln Lys Val Glu Glu Ser Lys Leu Lys Arg Asn Thr Arg
        915             920             925

Tyr Thr Val Ser Gly Phe Ile Ala His Ala Thr Asp Leu Glu Ile Val
    930             935             940

Val Ser Arg Tyr Gly Gln Glu Ile Lys Lys Val Val Gln Val Pro Tyr
945             950             955             960

Gly Glu Ala Phe Pro Leu Thr Ser Ser Gly Pro Val Cys Cys Ile Pro
            965             970             975

```
     His  Ser  Thr  Ser  Asn  Gly  Thr  Leu  Gly  Asn  Pro  His  Phe  Phe  Ser  Tyr
                    980                      985                      990

Ser  Ile  Asp  Val  Gly  Ala  Leu  Asp  Val  Asp  Thr  Asn  Pro  Gly  Ile  Glu
                    995                      1000                     1005

Phe  Gly  Leu  Arg  Ile  Val  Asn  Pro  Thr  Gly  Met  Ala  Arg  Val  Ser  Asn
                    1010                     1015                     1020

Leu  Glu  Ile  Arg  Glu  Asp  Arg  Pro  Leu  Ala  Ala  Asn  Glu  Ile  Arg  Gln
     1025                     1030                     1035                     1040

Val  Gln  Arg  Val  Ala  Arg  Asn  Trp  Arg  Thr  Glu  Tyr  Glu  Lys  Glu  Arg
                         1045                     1050                     1055

Ala  Glu  Val  Thr  Ser  Leu  Ile  Gln  Pro  Val  Ile  Asn  Arg  Ile  Asn  Gly
                    1060                     1065                     1070

Leu  Tyr  Asp  Asn  Gly  Asn  Trp  Asn  Gly  Ser  Ile  Arg  Ser  Asp  Ile  Ser
                    1075                     1080                     1085

Tyr  Gln  Asn  Ile  Asp  Ala  Ile  Val  Leu  Pro  Thr  Leu  Pro  Lys  Leu  Arg
                    1090                     1095                     1100

His  Trp  Phe  Met  Ser  Asp  Arg  Phe  Ser  Glu  Gln  Gly  Asp  Ile  Met  Ala
     1105                     1110                     1115                     1120

Lys  Phe  Gln  Gly  Ala  Leu  Asn  Arg  Ala  Tyr  Ala  Gln  Leu  Glu  Gln  Asn
                         1125                     1130                     1135

Thr  Leu  Leu  His  Asn  Gly  His  Phe  Thr  Lys  Asp  Ala  Ala  Asn  Trp  Thr
                    1140                     1145                     1150

Val  Glu  Gly  Asp  Ala  His  Gln  Val  Val  Leu  Glu  Asp  Gly  Lys  Arg  Val
                    1155                     1160                     1165

Leu  Arg  Leu  Pro  Asp  Trp  Ser  Ser  Val  Ser  Gln  Thr  Ile  Glu  Ile
                    1170                     1175                     1180

Glu  Asn  Phe  Asp  Pro  Asp  Lys  Glu  Tyr  Gln  Leu  Val  Phe  His  Gly  Gln
     1185                     1190                     1195                     1200

Gly  Glu  Gly  Thr  Val  Thr  Leu  Glu  His  Gly  Glu  Glu  Thr  Lys  Tyr  Ile
                         1205                     1210                     1215

Glu  Thr  His  Thr  His  His  Phe  Ala  Asn  Phe  Thr  Thr  Ser  Gln  Arg  Gln
                    1220                     1225                     1230

Gly  Leu  Thr  Phe  Glu  Ser  Asn  Lys  Val  Thr  Val  Thr  Ile  Ser  Ser  Glu
                    1235                     1240                     1245

Asp  Gly  Glu  Phe  Leu  Val  Asp  Asn  Ile  Ala  Leu  Val  Glu  Ala  Pro  Leu
                    1250                     1255                     1260

Pro  Thr  Asp  Asp  Gln  Asn  Ser  Glu  Gly  Asn  Thr  Ala  Ser  Ser  Thr  Asn
     1265                     1270                     1275                     1280

Ser  Asp  Thr  Ser  Met  Asn  Asn  Asn  Gln
                    1285
```

( 2 ) INFORMATION FOR SEQ ID NO:5:

( i ) SEQUENCE CHARACTERISTICS:
        ( A ) LENGTH: 295 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

```
ATCGATAAGC TTGATATCGA ATTCCTGCAG CCCGGGGGAT CCCGGCTACA TTAAATGAAG      60

TATATCCAGT AAATTATAAT GTATTATCTT CTGATGCTTT TCAACAATTA GATACAACAG     120

GTTTTAAAAG TAAATATGAT GAAATGATAA AAGCATTCGA AAAAAAATGG AAAAAAGGGG     180

CAAAAGGAAA AGACCTTTTA GATCTTGCAT GGACTTATAT AACTACAGGA GAAATTGACC     240
```

```
CTTTAAATGT AATTAAAGGT GTTTTATCTG TATTAACTTT AATTCCTGAA GTTGG          295
```

( 2 ) INFORMATION FOR SEQ ID NO:6:

( i ) SEQUENCE CHARACTERISTICS:
        ( A ) LENGTH: 285 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

```
AATTTTGTCT AAAACCATTC CATTTTTATC ATTATGTTGG ATTTGAAGAG TATGGTTACC      60
TTCTGTAATT GTATATGAAC CTATTGTATA TAAATCATAA TTTTCACCAA TATTACCGGT     120
TACATAACCG TTGTGTGAAG TAGGTATATT AAGCGTTTGC AGTTCCTGAT TATCTAAACG     180
AAAATAACCT TTTGTTCCTT GGGTACTGGC ATAACGTATA CGAATGGTAT ATTGAGCTGT     240
TTTTGAAGC ATGAAATTCG AATATAATGT TTGCTGGTTT CCAGA                     285
```

COMPOSITIONS AND METHODS FOR THE CONTROL OF FLUKES

CROSS-REFERENCE TO A RELATED APPLICATION

This is a continuation-in-part of application Ser. No. 07/565,544, filed on Aug. 10, 1990, now abandoned which is a continuation-in-part of application Ser. No. 07/084,653, filed on Aug. 12, 1987, now U.S. Pat. No. 4,948,734. This is also a continuation-in-part of Ser. No. 07/557,246, filed Jul. 24, 1990 which is a continuation-in-part of Ser. No. 07/535,810, filed Jun. 11, 1990, now abandoned which is a continuation-in-part of Ser. No. 07/084,653, filed Aug. 12, 1987, now U.S. Pat. No. 4,948,734. This is also a continuation-in-part application of Ser. No. 07/558,738 filed on Jul. 27, 1990, now U.S. Pat. No. 5,151,363.

BACKGROUND OF THE INVENTION

Flukes belong to subclass Digenea, class Trematoda in the phylum Platyhelminthes. These digeneans all have an intermediate host and are found exclusively in vertebrates, including man. Families which have members of considerable veterinary importance are Fasciolidae, Dicrocoeliidae, Paramphistomatidae, and Schistosomatidae.

The adult trematode flukes occur primarily in the bile ducts, alimentary tract, and vascular system. Most flukes are flattened dorso-ventrally, have a blind alimentary tract, suckers for attachment, and are hermaphroditic. Depending on the predilection site, the eggs pass out of the final host, usually in faeces or urine, and the larval stages develop in a molluscan intermediate host. For a few species, a second intermediate host is involved, but the mollusc is essential for all members of the group. They are worldwide in their distribution.

Several clinical syndromes may be associated with liver fluke (Fasciola sp.) infection, depending on the numbers and stage of development of the parasite and on the presence or absence of certain bacteria (*Clostridium novyi*). Acute fluke disease occurs during invasion of the liver by recently ingested metacercariae. In heavy invasions, the trauma inflicted by the maritas tunneling about in the liver and consequent inflammatory reaction result in highly fatal clinical illness characterized by abdominal pain with a disinclination to move. Sheep can die very quickly due to focal liver necrosis and extensive subcutaneous hemorrhage.

Subacute and chronic fluke disease is associated with the presence of adult trematodes in the bile ducts and characterized by the classical clinical signs of liver fluke infection. There is gradual loss of condition, progressive weakness, anemia, and hypoproteinemia with development of edematous subcutaneous swellings, especially in the intermandibular space and over the abdomen. There is considerable economic waste in cattle livers condemned as unfit for human consumption; destructive migrations in the livers of sheep and goats virtually preclude small ruminant production in endemic areas.

Light infections of flukes may not elicit clinical effects, but the parasites can have a significant effect on production due to an impairment of appetite and to their effect on post-absorptive metabolism of protein, carbohydrates, and minerals.

*Dicrocoelium dendriticum*, a fluke in the family Dicrocoeliidae, of economic importance in sheep, cattle, and pigs, has a life cycle adapted to a sequence of hosts that frequent dry habitats. Adults are parasites of the bile ducts of their hosts and have life cycles utilizing snails and ants as their intermediate hosts. Although clinical illness is absent in young animals, these trematodes are long-lived and the pathological changes in the liver increase in severity and extent with the duration of the infection. Ergo, in older sheep, *D. dendriticum* infection causes progressive hepatic cirrhosis manifested clinically as cachexia, lowered wool production, decreased lactation, and premature aging. Essentially, it makes sheep husbandry unprofitable by curtailing the reproductive life of the ewe flock. *Platynosomum fastosum*, another member of this family, is a parasite of the bile and pancreatic ducts of cats, occurring in the southern U.S. and the Caribbean; infection is acquired by eating lizards containing metacercariae.

Control of fascioliasis may be approached in two ways: by reducing populations of the intermediate snail host or by using anthelmintics.

Theoretically, aquatic snails can be controlled by draining swamps or by broadcasting molluscicides on the snail-infested waters, but the continued existence of flukes where they have always been indicates that snail control measures are impracticable in many cases. Areas connected by streams with other snail-infested regions are generally not amenable to snail control measures.

Anthelmintic medication in the U.S. currently consists primarily of albendazole, which is available in only a few states where *Fasciola hepatica* poses a serious problem. Special dispensation is required to treat sheep with albendazole elsewhere in the U.S. Other effective flukicides—diamphenethide, nitroxynil, oxyclozanide, rafoxanide, and triclabendazole—are not available in the U.S.

Regular use of chemicals to control unwanted organisms can select for drug resistant strains. This has occurred in many species of economically important pests. The development of drug resistance necessitates a continuing search for new control agents having different modes of action.

The bacterium *Bacillus thuringiensis* (B.t.) produces δ-endotoxin polypeptides that have been shown to have activity against a number of insect species. These toxins are deposited as crystalline inclusions within the organism. Many strains of B.t. produce crystalline inclusions with no demonstrated toxicit to any insect tested.

A small number of research articles have been published about the effects of δ-endotoxins from *B. thuringiensis* species on the viability of nematode eggs. Bottjer, Bone, and Gill (Experimental Parasitology 60:239-244, 1985) have reported that *B.t. kurstaki* and *B.t. israelensis* were toxic in vitro to eggs of the nematode *Trichostrongylus colubriformis*. In addition, 28 other B.t. strains were tested with widely variable toxicities. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against certain nematodes. Beta exotoxin is a generalized cytotoxic agent with little or no specificity. Also, H. Ciordia and W. E. Bizzell (Jour. of Parasitology 47:41 [abstract]1961) gave a preliminary report on the effects of *B. thuringiensis* on some cattle nematodes.

At the present time there is a need to have more effective means to control liver flukes that cause considerable damage to susceptible hosts. Advantageously, such effective means would employ biological agents.

BRIEF SUMMARY OF THE INVENTION

The subject invention concerns isolates and genes of *Bacillus thuringiensis* that are active against flukes. Specifically, the compounds of the subject invention have been shown to be highly active against the liver fluke *Fasciola hepatica*.

the B.t. isolates used according to the subject invention can be grown and the δ-endotoxin that is produced recovered by standard procedures and as further described herein. The recovered toxin or the B.t. isolates themselves can be formulated using standard procedures associated with the use of flukicidal products.

Among the B.t. isolates which can be used according to the subject invention are B.t. PS17, B.t. PS33F2, B.t. PS63B, B.t. PS69D1, B.t. PS80JJ1, B.t. PS158D5, B.t. PS167P, B.t. PS169E, B.t. PS177F1, B.t. PS177G, B.t. PS204G4, and B.t. PS204G6.

The subject invention further concerns the use of genes cloned from *Bacillus thuringiensis* isolates. Specifically exemplified are four genes cloned from the B.t. isolate designated B.t. PS17. The genes designated PS17d, PS17b, PS17a and PS17e, encode *Bacillus thuringiensis* δ-endotoxins which are active against flukes. The genes can be transferred to suitable hosts via a recombinant DNA vector. The transformed hosts which express the flukicidal toxins can be used in methods to control flukes. Also, the toxins expressed by these microbes can be recovered and used in fluke control procedures.

BRIEF DESCRIPTION OF THE DRAWING

Seq. ID No. 1 discloses the DNA of PS17a.

Seq. ID No. 2 discloses the amino sequence of the toxin encoded by PS17a.

Seq. ID No. 3 discloses the DNA of PS17b.

Seq. ID No. 4 discloses the amino acid sequence of the toxin encoded by PS17b.

Seq. ID No. 5 is the aminoterminal nucleotide sequence of isolate PS33F2.

Seq. ID No. 6 is the internal nucleotide sequence of isolate PS33F2.

DETAILED DISCLOSURE OF THE INVENTION

Isolates which can be used according to the subject invention have been deposited in the permanent collection of the Agricultural Research Service Patent Culture Collection (NRRL), Northern Regional Research Center, 1915 North University Street, Peoria, Ill. 61604, USA. The accession numbers are as follows:

| Culture | Repository No. | Deposit Date |
|---|---|---|
| B.t. PS17 | NRRL B-18243 | July 28, 1987 |
| B.t. PS33F2 | NRRL B-18244 | July 28, 1987 |
| B.t. PS52A1 | NRRL B-18245 | July 28, 1987 |
| B.t. PS63B | NRRL B-18246 | July 28, 1987 |
| B.t. PS69D1 | NRRL B-18247 | July 28, 1987 |
| E. coli NM522 (pMYC1627) | NRRL B-18651 | May 11, 1990 |
| E. coli NM522 (pMYC1628) | NRRL B-18652 | May 11, 1990 |
| B.t. PS80JJ1 | NRRL B-18679 | July 17, 1990 |
| B.t. PS158D5 | NRRL B-18680 | July 17, 1990 |
| B.t. PS167P | NRRL B-18681 | July 17, 1990 |
| B.t. PS169E | NRRL B-18682 | July 17, 1990 |
| B.t. PS177F1 | NRRL B-18683 | July 17, 1990 |
| B.t. PS177G | NRRL B-18684 | July 17, 1990 |
| B.t. PS204G4 | NRRL B-18685 | July 17, 1990 |

-continued

| Culture | Repository No. | Deposit Date |
|---|---|---|
| B.t. PS204G6 | NRRL B-18686 | July 17, 1990 |

The toxin genes used according to the subject invention can be obtained, for example, from the *B. thuringiensis* isolate designated PS17. As shown above, a subculture of B.t. PS17 and the *E. coli* host harboring the toxin genes of the invention have been deposited.

All of the above-listed cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

As described herein, B.t. isolates of the invention have activity against liver flukes. It is expected that these isolates would be active against other flukes as disclosed herein.

The B.t. toxins of the invention can be administered orally in a unit dosage from such as a capsule, bolus or tablet, or as a liquid drench when used against flukes in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divide diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distiller's dried grains, corn meal, citrus meal, fermentation residues, ground oyster shells, wheat shorts, molasses solubles, corn cob meal, edible beam mill feed, soya grits, crushed limestone and the like.

In addition to having activity against flukes within the digestive tract of mammals, spores from B.t. isolates of the invention will pass through the animals' digestive tract, germinate and multiply in the feces, and thereby provide additional control of fluke larva which hatch and multiply therein.

The gene(s) from the B.t. isolates of the subject invention can be introduced into microbes capable of occupying, surviving in, and proliferating in the phytosphere of plants according to the procedure of European Patent Application 0 200 344. Upon ingestion of such a plant by an animal hosting a fluke, the fluke-active toxin becomes available in the animal host to control the fluke infestation.

The toxin genes from the isolates of the subject invention can be introduced into a wide variety of microbial hosts. Expression of the toxin gene results, directly or indirectly, in the intracellular production and maintenance of the toxin. With suitable hosts, e.g., Pseudomonas, the microbes can be applied to the situs of flukes where they will proliferate and be ingested by the flukes. The result is a control of the flukes. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the toxin from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are known and available for introducing the B.t. genes expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for flukicidal activity.

Suitable host cells, where the toxin-containing cells will be treated to prolong the activity of the toxin in the cell when the treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the flukicide in the host, and the presence of auxiliary genetic capabilities. Characteristics of interest for use as a fluke toxin microcapsule include protective qualities for the toxin, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. fluke toxin gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The fluke toxin concentration will vary widely depending upon the nature of the particular formulation, particularly whether it is a concentrate or to be used directly. The toxin will be present in at least 1% by weight and may be 100% by weight. The dry formulations will have from about 1-95% by weight of the flukicide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the flukes, e.g., plants, soil or water, by spraying, dusting, sprinkling, or the like.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (gly) | GGL |

-continued

Termination signal  TAJ

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively
QR = AG if S is T or C
J = A or G
K = T or C
L = A, T, C or G
M = A, C or T The above shows that the novel amino acid sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

The methods and compositions of the subject invention can be used to control liver flukes, which can parasitize vertebrates. Specifically, the invention can be used to control flukes in humans, livestock, domestic pets, and other animals. As used herein, the term "livestock" can include, for example, sheep, cattle, pigs, and goats. The methods and compositions of the subject invention may be used to control immature and adult flukes. The methods of control include, but are not limited to, pasture treatment (for vertebrate and intermediate hosts); liposomes or other carriers for delivering the toxins to the liver or bile ducts; and treatment of free-living forms of the flukes in the gastrointestinal tracts of vertebrate hosts. The flukicidal B.t. toxins described herein may be used alone, or in rotation or combination with other flukicides such as, for example, albendazole.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates

A subculture of B.t. isolate can be used to inoculate the following medium, a peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Purification of Protein and Amino Acid Sequencing

The B.t. isolates PS33F2, PS63B, PS52A1, and PS69D1 were cultured as described in Example 1. The parasporal inclusion bodies were partially purified by sodium bromide (28-38%) isopycnic gradient centrifugation (Pfannenstiel, M. A., E. J. Ross, V. C. Kramer, and K. W. Nickerson [1984] FEMS Microbiol. Lett. 21:39). Toxic proteins were bound to PVDF membranes (Millipore, Bedford, Mass.) by western blotting techniques (Towbin, H., T. Staehlelin, and K. Gordon [1979] Proc. Natl. Acad. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] Meth. Enzymol. 91:399). The sequences obtained were:

PS33F2  A T L N E V Y P V N
PS52A1  M I I D S K T T L P R H S L I N T
PS63B   Q L Q A Q P L I P Y N V L A
PS69D1  M I L G N G K T L P K H I R L A H I F A T Q N S

In addition, internal amino acid sequence data were derived for PS63B. The toxin protein was partially digested with *Staphylococcus aureus* V8 protease (Sigma Chem. Co., St. Louis, Mo.) essentially as described (Cleveland, D. W., S. G. Fischer, M. W. Kirschner, and U. K. Laemmli [1977] J. Biol. Chem. 252:1102). The digested material was blotted onto PVDF membrane and a ca. 28 kDa limit peptide was selected for N-terminal sequencing as described above. The sequence obtained was:

63B(2) V Q R I L D E K L S F Q L I K

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from B.t. isolates. RFLP analysis of restricted total cellular DNA using radiolabeled oligonucleotide probes has elucidated different genes or gene fragments. The following table reviews the data.

TABLE 1

| B.t. Isolate | Size (kb) restriction fragment hybridizing with probe A under EcoRI restriction Probe A |
|---|---|
| PS52A1 | 3.5 |
| PS63B | 5.2 |
| PS69D1 | 6.4 |

Probe A has the following sequence: 5'-CAATTACAAGCACAACCTTTA-3'

EXAMPLE 3

Polymerase Chain Reaction (PCR) and Partial Nucleotide Sequence of a δ-Endotoxin Gene from PS33F2

The δ-endotoxin gene identified in PS33F2 was further characterized by the polymerase chain reaction (PCR) using a DNA Thermal Cycles, a GeneAmp DNA amplification kit (Perkin-Elmer Corp., Norwalk, Conn.), and standard reactions as specified by the manufacturer. The forward primer was:

5' CGGGATCCCGC A/T AC A/T TTAAATGAAGT A/T TAT 3'

The reverse primer was:

5' GCAAGCGGCCGCTTATGGAATAAATTCAATT
C/T T/G A/G TC T/A A 3'

The aminoterminal and internal nucleotide sequences are shown in Seq. ID No. 5 and Seq. ID. No. 6.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

EXAMPLE 4

Purification and N-Terminal Sequencing of B.t. Isolate PS17

One *Bacillus thuringiensis* (B.t.) isolate which can be used as the source of flukicidal toxin protein according to the subject invention is identified as B.t. strain PS17. The culture can be grown using standard media and fermentation techniques well known in the art. The toxin protein inclusions were harvested by standard sedimentation centrifugation. The recovered protein inclusions were partially purified by sodium bromide (28-38%) isopycnic gradient centrifugation (Pfannenstiel, M. A., E. J. Ross, V. C. Kramer, and K. W. Nickerson [1984] FEMS Microbiol. Lett. 21:39). Thereafter the individual toxin proteins were resolved by solubilizing the crystalline protein complex in an alkali buffer and fractionating the individual proteins by DEAE-sepharose CL-6B (Sigma Chem. Co., St. Louis, Mo.) chromatography by step-wise increments of increasing concentrations of an NaCl-containing buffer (Reichenberg, D., in *Ion Exchangers in Organic and Biochemistry* [C. Calmon and T. R. E. Kressman, eds.], Interscience, New York, 1957). Fractions containing the toxin protein were bound to PVDF membrane (Millipore, Bedford, Mass.) by western blotting techniques (Towbin, H., T. Staehelin, and K. Gordon [1979] Proc. Natl. Acad. Sci. USA 76:4350) and the N-terminal amino acids were determined by the standard Edman reaction with an automated gas-phase sequenator (Hunkapiller, M. W., R. M. Hewick, W. L. Dreyer, and L. E. Hood [1983] Meth. Enzymol. 91:399). From these sequence data an oligonucleotide probe can be designed by utilizing a codon frequency table assembled from available nucleotide sequence data of other B.t. toxin genes. A probe was synthesized on an Applied Biosystems, Inc. DNA synthesis machine.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 5

Cloning of Four Toxin Genes from B.t. PS17 and Transformation into *Escherichia coli*

Total cellular DNA was prepared by growing the cells B.t. PS17 to a low optical density ($OD_{600} = 1.0$) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe derived from the N-Terminal amino acid sequence of purified 130 kDa protein from PS17. The sequence of the oligonucleotide synthesized is (GCAATTTTAAATGAAT-TATATCC). Results showed that the hybridizing EcoRI fragments of PS17 are 5.0 kb, 4.5 kb, 2.7 kb and 1.8 kb in size, presumptively identifying at least four toxin genes, PS17d, PS17b, PS17a and PS17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip ™ ion exchange column (Schleicher and Schuel, Keene, N.H.). The isolated Sau3A fragments were ligated into LambdaGEM-11 ™ (PROMEGA). The packaged phage were plated on KW251 *E. coli* cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (PS17b) or the 2.7 kb (PS17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac. The ligation mix was introduced by transformation into NM522 competent *E. coli* cells and plated on LB agar containing ampicillin, isopropyl-(Beta)-D-thiogalactoside (IPTG) and 5-Bromo-4-Chloro-3-indolyl-(Beta)-D-galactoside (XGAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York.

The restriction enzymes disclosed herein can be purchased from Bethesda Research Laboratories, Gaithersburg, Md., or New England Biolabs, Beverly, Mass. The enzymes are used according to the instructions provided by the supplier.

The PS17 toxin genes were subcloned into the shuttle vector pHT3101 (Lereclus, D. et al. [1989] FEMS Microbiol. Lett. 60:211-218) using standard methods for expression in B.t. Briefly, SalI fragments containing the PS17b and a toxin genes were isolated from pMYC1628 and pMYC1627, respectively, by preparative agarose gel electrophoresis, electroelution, and concentrated, as described above. These concentrated fragments were ligated into SalI-cleaved and phosphatased pHT3101.

The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the PS17a and b toxin genes, respectively. These plasmids were transformed into the acrystalliferous B.t. strain, HD-1 cryB (Purdue University, Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 6

Activity Against *Fasciola hepatica*

Toxins produced by wild type B.t. isolates and recombinant microbes expressing B.t. proteins were tested for their flukicidal activity.

In vitro culture (37° C., 5% $CO_2$) was according to modification of the method of Ibarra and Jenkins (Z. Parasitenkd. 70:655-661, 1984). Culture media consisted of RPMI (7.5 pH) with 50% v/v rabbit serum and 2% v/v rabbit RBC.

Test compounds

In the experiments described below, the effects of various substances on liver flukes were tested and compared. As used herein, Compound PS17 refers to toxin recovered and purified from cultures of B.t. PS17 as described above. Compound PS17a refers to toxin recovered and purified from cultures of the recombinant microbe which has been transformed with the B.t. gene designated B.t. PS17a. Compound C, is a formulation blank used as a negative control. ABZ refers to the drug Albendazole, which can be obtained from SmithKline Beecham, Lincoln, Nebr. Compounds PS17, PS17a, C, D, and E were added directly to media at 100 ppm; ABZ was dissolved in 100 μl absolute ethanol prior to addition to media.

Criteria for efficacy

Flukes were examined hourly for 3-8 hours and then once or twice daily for effects of drug treatment as evidenced by death, motility disturbances, or morphologic changes as compared to untreated control flukes, using an inverted microscope at 40×.

Three-week-old *Fasciola hepatica* removed from the livers of experimentally infected rabbits were cultured in vitro for 5 days in 1.6 cm Linbro culture plate wells (2 ml media; 4-6 flukes/well). After 5 days incubation, flukes were transferred to media containing Compound PS17a (100 ppm; 5 flukes), Compound PS17 (100 ppm; 6 flukes), or to untreated control media (4 flukes). All flukes were dead in Compound PS17a by 18 hours. In Compound PS17 only one fluke was alive (sluggish) at 24 hours compared to three live flukes in the media control (Table 1). All flukes were fixed and stained for morphologic study; no apparent microscopic changes were observed except those attributable to analysis of dead flukes. During the 5-day pre-culture period, flukes remained active and were observed ingesting RBC's from the media, with an apparently active digestive function.

TABLE 1

| | Number of living immature F. hepatica (3 weeks old), rabbit origin | | |
|---|---|---|---|
| Observation time | Compound PS17a 100 ppm | Compound PS17 100 ppm | Media control |
| 0 | 5 | 6 | 4 |
| 5 minutes | 5 | 6 | 4 |
| 1 hour | 5 | 6 | 4 |
| 2 hours | 5 | 6 | 4 |
| 3 hours | 5 | 6 | 4 |
| 6 hours | 5 | 6 | 4 |
| 8 hours | 5 | 6 | 4 |
| 18 hours | 0 | 4 (sluggish) | 3 |
| 24 hours | | 1 (sluggish) | 3 |

Four mature flukes recovered from a naturally infected calf were separately cultured in vitro in 25 cm² tissue culture flasks in 5 ml media for 24 hours and then transferred to similar flasks containing Compound PS17a (100 ppm), Compound PS17 (100 ppm), ABZ (10 ppm) or untreated media (Table 2). Flukes in Compound PS17a died between 10 and 18 hours, in Compound PS17 between 18 and 20 hours, and in ABZ by 64 hours. The media control fluke died in 72 hours in association with contamination of media as evidenced by turbidity and yellow media coloration.

These flukes were cultured in RPMI 49%+Rabbit serum 49%+Rabbit RBC 2% for 5 days prior to trial initiation. The experiment terminated after 24 hours, and all flukes were fixed for morphological study. Behavior of flukes prior to mortality included less activity and oral suckers directed to the surface of the media. At death, the body is contracted, then relaxed prior to decomposition.

TABLE 2

| | Number of living mature flukes | | | |
|---|---|---|---|---|
| Observation time | Compound PS17a 100 ppm | Compound PS17 100 ppm | Albendazole 10 ppm | Media Control |
| 0 | 1 | 1 | 1 | 1 |
| 5 min. | 1 | 1 | 1 | 1 |
| 1 hour | 1 | 1 | 1 | 1 |
| 2 hours | 1 | 1 | 1 | 1 |
| 3 hours | 1 | 1 | 1 | 1 |
| 6 hours | 1 | 1 | 1 | 1 |
| 8 hours | 1 | 1 | 1 | 1 |
| 10 hours | 1 | 1 | 1 | 1 |
| 18 hours | 0 | 1* | 1 | 1 |
| 20 hours | | 0 | 1 | 1 |
| 31 hours | | | 1 | 1 |
| 60 hours | | | 1 | 1 |
| 64 hours | | | 0 | 1 |
| 72 hours | | | | 0** |

*Sluggish movement.
**Contracted folded body without movement, with turbidity of the media.

EXAMPLE 5

An additional experiment was done to test the efficacy of Compounds PS17 and PS17a against *F. hepatica* as compared to albendazole (ABZ), a drug with known efficacy (positive control) and an untreated media control. Tests were done against 1) mature flukes recovered from naturally infected calves and 2) immature 5-week-old rabbit origin flukes.

Immature flukes

Five-week-old immature *F. hepatica* were recovered from experimentally infected rabbit livers and placed in culture media overnight (1.6 cm Linbro culture plates, 2-3 flukes per well) in triplicate. Flukes were then transferred to similar Linbro plates containing 2 ml of Compound PS17a (100 ppm), Compound PS17 (100 ppm), albendazole (ABZ, 10 ppm), or untreated media (Table 3). In Compound PS17a, 7 of 7 flukes had died by 20 hours; sluggish movement was noted at 8-hours-post-exposure. In Compound PS17, mortality (2 of 7 flukes) and sluggish movement of remaining flukes was noted at 20 hours; at 31 hours 5 of 7 flukes were dead; at 48 hours all flukes were dead. In the ABZ positive control, 1 of 7 flukes was dead at 20 hours, 4 had died by 31 hours, and remaining flukes died by 60 hours. In untreated control media, 2 of 7 flukes had died at 31 hours, 3 at 48 hours, 4 at 55 hours, 5 at 60 hours, and 7 of 7 were dead by 72 hours. (NOTE: Superficial layers of some wells became turbid at 35 hours post-exposure; all flukes were washed in RPMI and transferred to wells containing fresh media at original drug concentrations).

Mature flukes

Mature flukes recovered from 3 calf livers that had been condemned due to fascioliasis (Roucher's Meat Packing, Plaquemine, La.) were washed and held in sterile saline (for 2-3 hours) and four flukes were placed in each of two 25 ml tissue culture flasks containing Compound PS17a (100 ppm); Compound PS17 (100 ppm); ABZ (10 ppm) or untreated control media (Table 4). All flukes were dead in Compound PS17a by 10-11 hours and in Compound PS17 by 20 hours. In ABZ, flukes died by 48-54 hours. In control media, 2 flukes died by 48 hours; all flukes died by 66 hours. (NOTE: Contamination in flasks was noted at 31-48 hours).

TABLE 3

| | Number of living immature flukes, rabbit origin (5 weeks old) | | | | | | | | | | | |
|---|---|---|---|---|---|---|---|---|---|---|---|---|
| | Compound PS17a 100 ppm | | | Compound PS17 100 ppm | | | Albendazole 10 ppm | | | Media control | | |
| Obser. time | W1 | W2 | W3 | W1 | W2 | W3 | W1 | W2 | W3 | W1 | W2 | W3 |
| 0 | 2 | 2 | 3 | 2 | 2 | 3 | 2 | 2 | 2 | 2 | 2 | 3 |
| 5 min. | 2 | 2 | 3 | 2 | 2 | 3 | 2 | 2 | 2 | 2 | 2 | 3 |
| 1 hr. | 2 | 2 | 3 | 2 | 2 | 3 | 2 | 2 | 2 | 2 | 2 | 3 |
| 2 hr. | 2 | 2 | 3 | 2 | 2 | 3 | 2 | 2 | 2 | 2 | 2 | 3 |
| 3 hr. | 2 | 2 | 3 | 2 | 2 | 3 | 2 | 2 | 2 | 2 | 2 | 3 |
| 6 hr. | 2 | 2 | 3 | 2 | 2 | 3 | 2 | 2 | 2 | 2 | 2 | 3 |
| 8 hr. | 2* | 2* | 3* | 2 | 2 | 3 | 2 | 2 | 2 | 2 | 2 | 3 |
| 20 hr. | 0 | 0 | 0 | 2* | 2* | 1* | 2 | 2 | 2 | 2 | 2 | 3 |

TABLE 3-continued

| | Number of living immature flukes, rabbit origin (5 weeks old) | | | | | | | | | | | |
|---|---|---|---|---|---|---|---|---|---|---|---|---|
| | Compound PS17a 100 ppm | | | Compound PS17 100 ppm | | | Albendazole 10 ppm | | | Media control | | |
| Obser. time | W1 | W2 | W3 | W1 | W2 | W3 | W1 | W2 | W3 | W1 | W2 | W3 |
| 31 hr. | | | | 1* | 0 | 1* | 1 | 1 | 1 | 2 | 2 | 1 |
| 35 hr. | Note: Superficial layer of some wells appeared turbid. Media was changed and the flukes washed in RPMI only. Washed living flukes were transferred to new media with drugs at original concentrations. | | | | | | | | | | | |
| 48 hr. | | | | 0 | 0 | 0 | 1 | 1 | 1 | 1 | 2 | 1 |
| 55 hr. | | | | | | | 1 | 1 | 1 | 1 | 2 | |
| 60 hr. | | | | | | | 0 | 0 | 0 | 1* | 1* | 0 |
| 72 hr. | | | | | | | | | | 0 | 0 | 0 |

*Sluggish flukes.

TABLE 4

| | Effect on mature flukes (cattle origin) | | | | | | | |
|---|---|---|---|---|---|---|---|---|
| | Compound PS17a 100 ppm | | Compound PS17 100 ppm | | Albendazole | | Media control | |
| Obser. time | Flask 1 | Flask 2 | Flask 1 | Flask 2 | Flask 1 | Flask 2 | Flask 1 | Flask 2 |
| 0 | 4 | 4 | 4 | 4 | 4 | 4 | 4 | 4 |
| 5 min. | 4 | 4 | 4 | 4 | 4 | 4 | 4 | 4 |
| 1 hr. | 4 | 4 | 4 | 4 | 4 | 4 | 4 | 4 |
| 2 hr. | 4 | 4 | 4 | 4 | 4 | 4 | 4 | 4 |
| 3 hr. | 4 | 4 | 4 | 4 | 4 | 4 | 4 | 4 |
| 8 hr. | 4 | 4 | 4 | 4 | 4 | 4 | 4 | 4 |
| 10-11 hr. | 0 | 0 | 4 | 4 | 4 | 4 | 4 | 4 |
| 18 hr. | | | 4* | 4* | 4 | 4 | 4 | 4 |
| 20 hr. | | | 0 | 0 | 4 | 4 | 4 | 4 |
| 31 hr. | | | | | 4 | 4 | 4 | 4 |
| 48 hr. | | | | | 2 | 3 | 4 | 2 |
| | Note: Apparent contamination in flasks between 31-48 hours | | | | | | | |
| 54 hr. | | | | | 0 | 0 | 3 | 1 |
| 66 hr. | | | | | | | 0 | 0 |

*Sluggish movement.

EXAMPLE 6

Flukes were recovered from bile ducts of condemned calf livers and washed in sterile RPMI for 2-3 hours in groups of 10-20 flukes. Only one fluke was cultured in each well of 6-well Linbro tissue cultured plates (10 ml size), with each well containing 4 ml treated or untreated media. A formulation blank (Compound C) having no known flukicidal activity was also tested. Additional controls were added to identify sources of potential contamination, including a media control with 2% RBC and a media control without 2% RBC. The ABZ concentration was increased to 25 ppm. Control wells containing drug or media only were also included to control for contamination source.

This experiment included 12 replicates (Table 5); six of these replicates had corresponding wells with treated or untreated media only. For Compound PS17a, all 12 flukes died by 12 hours; weak movement was observed as early as 10 hours. All Compound PS17 flukes were dead by the 19 or 24 hour observation. Compound C fluke mortality was observed at 36-58 hours. For the media with 2% RBC and media without 2% RBC controls, one fluke was dead at 36 hours, two at 58 hours, and three at 72 hours; one fluke survived to 115 hours in media with 2% RBC.

For 8 of the 12 replicates and two of the 6 corresponding media controls, the media was electively changed in both fluke containing and non-fluke containing wells at 24 hours post-exposure. This extra handling procedure may have resulted in death of all flukes by 58 hours in 6 of the 8 replicates, apparently due to contamination as evidenced by turbidity and yellow color of media. Two fluke replicates in which media was changed in 24 hours did not become contaminated. None of the six media control (no fluke) replicates became contaminated during 115 hours of incubation.

TABLE 5

| | In vitro efficacy against adult *Fasciola hepatica* (cattle origin) | | | | | |
|---|---|---|---|---|---|---|
| Time Hr. | Compound PS17a 100 ppm | Compound PS17 100 ppm | Compound C 100 ppm | ABZ 25 ppm | Media No RBC | Media RBC |
| 1 | 12 | 12 | 12 | 12 | 12 | 12 |
| 2 | 12 | 12 | 12 | 12 | 12 | 12 |
| 3 | 12 | 12 | 12 | 12 | 12 | 12 |
| 10 | 12* | 12 | 12 | 12 | 12 | 12 |
| 14 | 0 | 12 | 12 | 12 | 12 | 12 |
| 19 | | 10 | 12 | 12 | 12 | 12 |
| 24 | | 0 | 12 | 11 | 12 | 12 |
| 36 | | | 8(5) | 7(4) | 11(5) | 11(5) |
| 44 | | | 4(3) | 5(2) | 11(5) | 11(5) |
| 58** | | | 0(0) | 2(0) | 5(0) | 5(0) |
| 74 | | | | 1 | 4 | 4 |
| 98 | | | | 0 | 1 | 2 |
| 115 | | | | | 0 | 1 |

*Weak movement only.
(Number of live flukes that were in replicates receiving media change at 25 hr.).
**All flukes in 6 of 8 replicates that received media change at 24 hr. were dead at 58 hours due to contamination, probably related to additional handling. Two media control replicates changed at 24 hours were not contaminated.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling flukes, said method comprising contacting said flukes with a flukicidally effective amount of a toxin from a wild-type *Bacillus thuringiensis* PS17 or a toxin encoded by a *Bacillus thuringiensis* PS17 gene which has been transformed into and expressed in a recombinant host.

2. The method, according to claim 1, wherein said recombinant host is selected from the group consisting of *Escherichia coli* NM522 (pMYC1627) and *Escherichia coli* NM522 (pMYC1628).

3. The method, according to claim 1, wherein said gene is selected from the group consisting of PS17a, PS17b, PS17d, PS17e.

4. The method, according to claim 3, wherein said gene is PS17a and has the sequence shown in SEQ. ID. No. 1.

5. The method, according to claim 3, wherein said gene is PS17 b and has the sequence shown in SEQ. ID. No. 3.

6. The method, according to claim 1, wherein said fluke is *Fasciola hepatica*.

7. The method, according to claim 1, which further comprises administration of one or more additional flukicidal compounds.

8. The method, according to claim 7, wherein said additional flukicidal compound is albendazole.

9. A flukicidal composition comprising a wild-type *Bacillus thuringiensis* PS17, or a toxin encoded by a *Bacillus thuringiensis* PS17 gene which has been transformed into and expressed in a recombinant host; said composition further comprising the flukicidal compound albendazole.

* * * * *

UNITED STATES PATENT AND TRADEMARK OFFICE
CERTIFICATE OF CORRECTION

PATENT NO. : 5,262,399
DATED : November 16, 1993
INVENTOR(S) : Leslie A. Hickle et al It is certified that error appears in the above-indentified patent and that said Letters Patent is hereby corrected as shown below:

Column 2, line 48, delete "toxicit" and insert —toxicity—
Column 3, line 10, delete "the" and insert —The—
Column 3, lines 17-18, after "B.t. PS33F2" insert —B.t. PS52A1—
Column 5, line 40, delete "edible beam" and insert —edible bean—
Column 18, line 54 (Table 5), delete "8(5)" insert --8(5)†--.
Column 18, line 59, insert befor "(Number" a "†".

Signed and Sealed this

Thirty-first Day of May, 1994

Attest:

BRUCE LEHMAN

*Attesting Officer*     Commissioner of Patents and Trademarks